United States Patent [19]

Hirshaut

[11] 4,072,577
[45] Feb. 7, 1978

[54] METHOD AND MINIATURIZED APPARATUS FOR CULTIVATING BACTERIA

[75] Inventor: Yashar Hirshaut, Lawrence, N.Y.

[73] Assignees: Samson Helfgott, Far Rockaway; Jack W. Benjamin, Rosedale, both of N.Y.

[21] Appl. No.: 475,054

[22] Filed: May 31, 1974

[51] Int. Cl.² .......................... C12B 1/00; C12K 1/04
[52] U.S. Cl. ..................................... 195/104; 195/139
[58] Field of Search ....................... 195/139, 104, 120

[56] References Cited

U.S. PATENT DOCUMENTS

| | | | |
|---|---|---|---|
| 2,348,448 | 5/1944 | Brewer | 195/139 |
| 3,158,553 | 11/1964 | Carski | 195/139 |
| 3,297,184 | 1/1967 | Andelin | 195/139 |
| 3,474,004 | 10/1969 | Fink | 195/139 |
| 3,597,326 | 8/1971 | Liner | 195/139 |
| 3,630,849 | 12/1971 | Land | 195/139 |
| 3,713,985 | 1/1973 | Astle | 195/103.5 M |
| 3,728,227 | 4/1973 | Elson et al. | 195/127 |
| 3,769,936 | 11/1973 | Swanson et al. | 195/139 |
| 3,808,103 | 4/1974 | Buissiere | 195/139 |
| 3,816,264 | 6/1974 | Winter et al. | 195/139 |
| 3,826,717 | 7/1974 | Gilbert et al. | 195/103.5 K |

Primary Examiner—Alvin E. Tanenholtz
Assistant Examiner—Robert J. Warden
Attorney, Agent, or Firm—Samson Helfgott; Jack W. Benjamin

[57] ABSTRACT

The present invention is directed to miniaturized, microbiological culture dishes, for example in the order of approximately 5 mm. in diameter and 5 mm. in depth, as well as a novel method and apparatus for cultivating the growth of bacteria. The culture dishes each contain a prepackaged culture medium and a sealed cover. In one embodiment the culture dishes are formed in an array on a frangible strip. The covers are removable to permit inoculation of the culture medium and are replaceable in a first condition to permit safe transport thereof. During incubation the covers are placed in a second condition to facilitate an indirect flow of air to the inoculated culture medium without allowing cross contamination between adjacent culture dishes. Several different dispensers are disclosed for transporting a plurality of culture dishes both before and after inoculation of the culture medium therein. A master support rack in combination with a single master cover that permits indirect air flow without cross contamination is also provided for large scale testing procedures. There is also disclosed a novel, double ended tool that is packaged in a sterilized, frangible container and which has a swab at one end for inoculating the culture medium. The other end of the tool is provided with a loop for streaking the culture medium.

27 Claims, 21 Drawing Figures

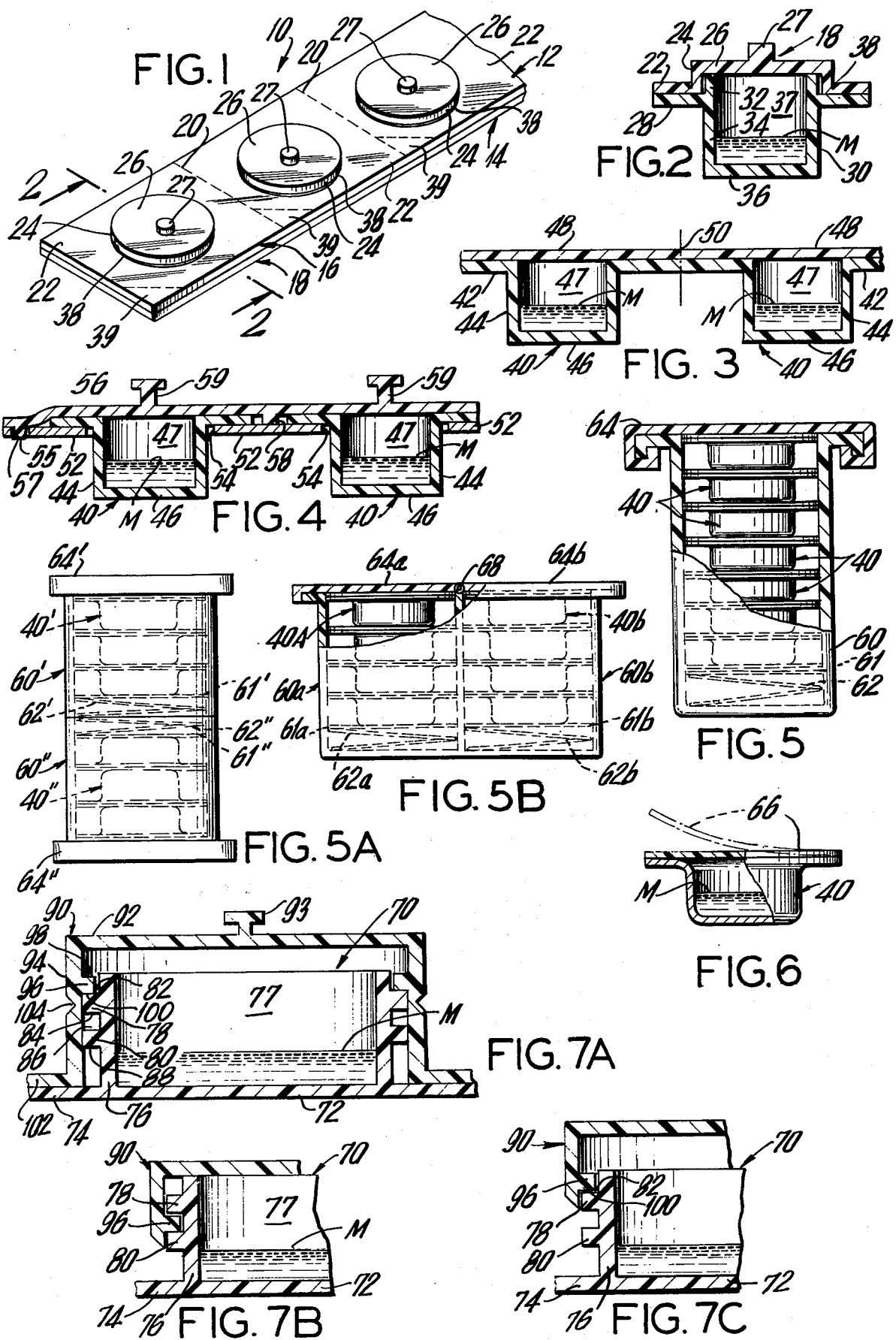

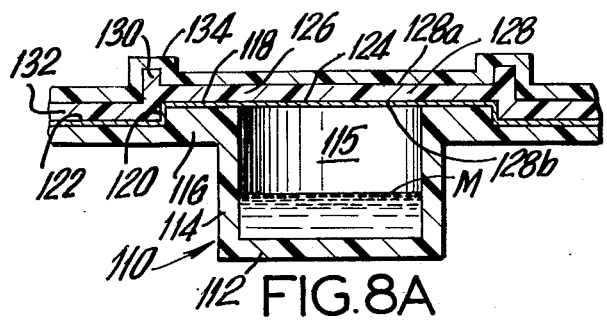
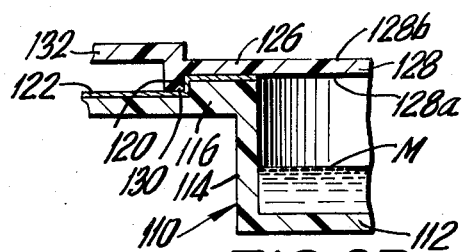
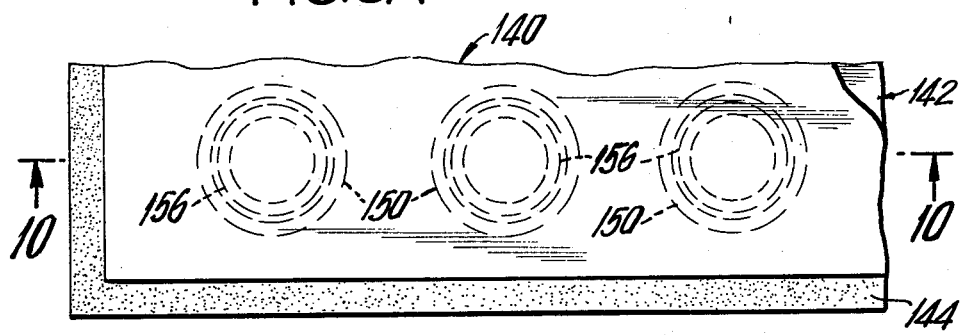
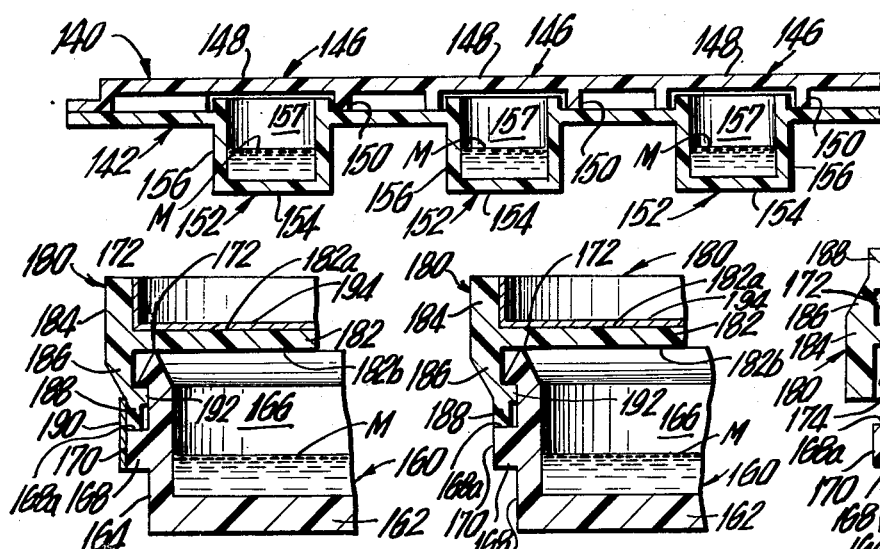
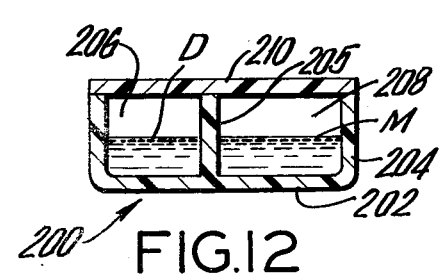
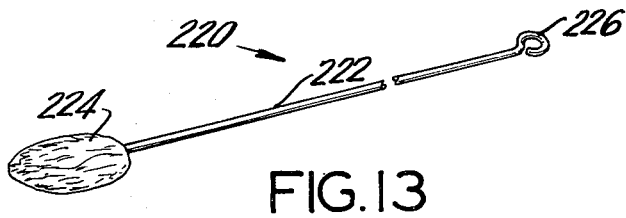
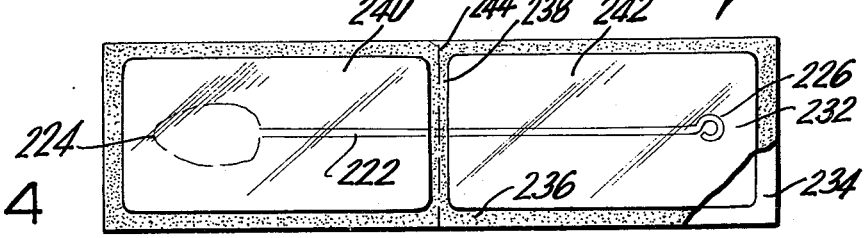

METHOD AND MINIATURIZED APPARATUS FOR CULTIVATING BACTERIA

BACKGROUND OF THE INVENTION

1. Field of the Invention

This invention relates generally to apparatus used in connection with the cultivation of bacteria and more particularly to miniaturized microbiological culture support devices and associated apparatus therefore as well as a method for using the apparatus with the devices comprising this invention.

2. Description of the Prior Art

One of the more important methods currently in use in the field of microbiology is the process for propagating organisms known as cultivation. In this process, bacteria are encouraged to grow by placing them on a suitable growth medium under environmental conditions permitting rapid replication. This process is widely utilized by practicing physicians in testing sputum and urine for the presence or absence of bacteria, for identifying the bacteria and for determining the sensitivity of bacteria to antibiotics. This process is also utilized in laboratories on a large scale for medical experimentation in order to determine the effects of various chemicals upon the growth of bacteria.

The process of cultivation of bacteria generally involves the utilization of a culture medium which is located within a culture dish. The culture medium contains all of the necessary nutrients for bacterial growth. In the prior art, a liquid medium is frequently used which has a gel consistency that is achieved by adding agar or silica gel. The culture medium is usually inoculated with the bacteria by utilizing a loop or a needle which contains the bacteria along its edge and by streaking the surface of the culture medium with the loop or needle. Frequently, a disposable cotton swab is first used for collecting the inoculum, for example from the patient's throat. The inoculum is then diluted in a diluant that is usually the same as the culture medium but without the agar. A disposable, plastic loop may then be used for inoculating the culture medium that contains the agar.

The prior art culture dish generally comprises a top or cover member and a loosely assembled bottom member having a well or receptacle portion. The bottom member contains the culture medium in the well thereof and the top overlaps the bottom member to allow an indirect flow of air into the wall during the cultivation process. Normally, the bottom and cover members are not sealed to each other so as to define individual units. The culture medium may be prepackaged in each dish and usually twelve dishes are provided in a sealed cellophane bag. Once the seal of the bag is broken the seal is open for all the dishes therein.

Before being used, the prior art dish with the culture medium therein is kept refrigerated in a sterile atmosphere to prevent contamination and bacterial growth. When it is desired to produce a culture growth, the dish is removed from its refrigerated storage and the top is removed in order to allow the loop or needle to streak the culture surface in the manner described above. The top is then quickly replaced over the bottom of the dish and the culture dish is placed in an incubator which is set at a predetermined temperature which will provide the proper growth environment. Following the incubation period, the dish is removed and uncovered and the culture medium examined to identify the various bacterial growth or colonies whose color, size and shape is characteristic for each type of bacteria.

In utilizing this process for urine culture, instead of using a loop or needle, a centrifuge tube or a syringe may be used to place the specimen on the growth medium. However, the complete process and the culture dish is generally the same as previously described.

The process of culture growth or cultivation is one of the most reliable tests for determining the presence of a specific type of bacteria. For example, growing a throat culture is a direct method for providing the physician with information concerning the specific type of bacteria present in the patient's throat. Such cultures are frequently the only way of determining whether streptococcus organisms or similar dangerous pathogens exist in the throat and whether or not antibiotics should be prescribed. More particularly, accurate identification of a specific bacteria permits the most effective antibiotic to be prescribed. Similarly, culture growth is an important means for identifying micro-organisms in a urinary tract infection.

While such tests may, in fact, be the most useful for the physician, it is uncommon that physicians will take a culture growth for each patient complaining of a sore throat or for each patient having a urinary infection. One reason is that, in order to maintain the proper equipment for culture growths, it is necessary for the physician to have a large and costly incubator, a large volume of refrigeration space, and a large supply of the loops and the culture dishes containing the culture medium. The culture dish used in the prior art practices is of relatively large size, typically about 10 cm. in diameter and about 1 cm. in depth. The medium is uniformly distributed in the prior art culture dish to a height of about 4 mm. Because of the large volume of culture medium needed to fill the dish the culture growth process involves a significant cost.

A particular drawback of the prior art structure is found in the requirement that the culture medium remains sterile. Because of the large size of the culture dishes it is inconvenient for physicians making house calls to carry along even a limited supply of the prior art culture dishes for making throat cultures or urine cultures when visiting patients.

In laboratory use, culture growth is not usually carried out on a substantially larger scale than normally employed by an individual physician. The analysis of the culture growth has, in the past been done on an individual culture dish basis by a skilled technician. The laboratory process is therefore costly and time consuming since each culture dish must be inoculated and analyzed individually. Furthermore, in laboratory use where a large quantity of culture dishes must be utilized in a single experiment, the space required for storing and incubating the culture dishes containing the growth medium becomes a problem and therefore severely limits the number of experiments utilizing this method.

While in other fields of medicine, such as immunology, the size of test equipment has been drastically reduced, miniaturization has not heretofore been achieved in microbiological culture growth. Basic problems in connection with miniaturization of the microbiological growth process are that the culture medium must remain in a sterile atmosphere prior to the inoculation and, during incubation, the culture medium must be protected from direct flow of air which may tend to cross-contaminate the culture medium with foreign organisms. On the other hand the culture medium must have an indirect flow of air after inoculation in order to achieve proper growth of the bacteria being tested. Problems relating to the safe transport of the inoculated culture medium must also be overcome.

SUMMARY OF THE INVENTION

According to the invention, there are provided miniaturized, microbiological culture dishes for retaining culture medium, each dish having its own sealed cover such that the culture medium contained within the dish is retained in a sterile atmosphere prior to use. The cover is easily removable from each dish to permit inoculation, of the culture medium contained in the culture dish such as by streaking with a suitable tool. After inoculation of the medium in the dish in the usual manner, the cover associated therewith is replaced to prevent cross-contamination with any adjacent culture dish and at the same time to permit an indirect flow of air to reach the culture medium. In one embodiment, where the culture dish must be transported through a distance, thereby causing a delay from the time of inoculation until incubation, the culture dish can be reclosed after inoculation and during transport. Upon reaching the place of incubation, inoculated culture medium is streaked and the cover is reoriented to prevent cross-contamination while permitting indirect flow of air to reach the medium during incubation. In another embodiment of the invention, the culture dishes are contained within an array which permits automated inoculation of the culture medium. The culture dishes can also be contained on a frangible strip that contains any given number, as desired.

Alternatively, individual or separate culture dishes can be maintained in and retained by a dual-purpose dispenser, which may also serve as a storage device for holding a plurality of culture dishes which have been inoculated and while they are transported back to the place of incubation. A holding device such as a master support rack having a single, master cover may also be provided for retaining a plurality of the miniaturized culture dishes during incubation.

It should be clearly understood that the present invention may include combinations of the various embodiments mentioned above. For example, individual covers for each culture dish may be used with the master support rack. In addition, adjacent wells or culture dishes may be used for the diluent and for the agar medium or each culture dish may have a double well. In such a construction the cover should be removable in stages so that the diluent can be exposed first and then the agar medium can be exposed so as to minimize the likelihood of cross-contamination.

The scope of the present invention also includes a novel, double ended tool having a swab at one end for use in the patient's throat and in the culture medium and a loop at the other end for streaking the culture medium. The tool is disposable after a single usage and preferably is packaged in a repturable, sterilized container having a separate compartment for each end of the tool. Thus, the loop end will remain sterile while the swab end is being used. The dual-purpose tool just described is particularly useful with the double or adjacent well embodiment of this invention in addition to the other embodiments.

It is therefore an object of the present invention to provide improved, miniaturized cultivation devices, as described above, for microbiological testing which avoid the aforementioned problems of the prior art.

A further object of the invention is to provide for the miniaturization of the culture dishes, as described above, utilized in microbiological culture growth.

Yet another object of the invention is to provide small, inexpensive and disposable culture dishes, as described above, that are adapted to retain a culture medium for use in microbiological testing.

Another object of the invention is to provide, as described above, an array of miniaturized culture dishes, each culture dish containing a culture medium, with the array being useful in automatic mass processing of culture growths.

Still a further object of the invention is to provide, as described above, a microbiological testing culture dish which is sterile and sealed prior to use, which is easily opened for inoculation, which is reclosable after inoculation for transporting to the incubation device and which includes means that permit indirect airflow into the culture medium during the incubation period.

Yet a further object of the present invention is to provide an array of disposable, miniaturized culture dishes as described above, each of which culture dish contains a culture medium and wherein each of the culture dishes is sealed prior to use, the seal being easily removable for inoculation either individually or automatically by mass inoculation devices, the cover of the culture dishes being easily replaced for incubation purposes and wherein an indirect flow of air is permitted to enter the culture dish while at the same time preventing a cross-contamination between adjacent culture dishes.

A further object of the invention is to provide an array of disposable, miniaturized culture dishes, as described above, which are initially in the form of a frangible strip whereby each culture dish can be detached from the remainder of the strip and whereby each culture dish can then be used individually.

Still a further object of the invention is to provide, as described above, means for storing and dispensing individual, sterile, disposable miniature culture dishes that are adapted for inoculation, and then storing the culture dishes after inoculation.

A particular object of the present invention is to provide an improved, miniaturized disposable culture dish, as described above, that is particularly adaptable to microbiological processes and which has a cover that is sealed to the dish in a first, "sterile" position, which cover is mounted on the culture dish in a second position after inoculation and during transport and which cover is mounted on the culture dish in still a third position that permits an indirect flow of air without cross-contamination during the incubation period.

Another specific object of this invention is to provide, as described above, an improved, disposable, miniaturized culture dish for use in the cultivation of bacteria and having a cover sealed thereto in a first position, the cover being provided with a removable sheet that seals an internal, sterile surface, the sheet being removable after inoculation so that the cover may be inverted and used for transport and incubation purposes, as described above.

Still another specific object of this invention is to provide a double ended combination swab and streaking tool that may be packaged in an individual, sterile container.

These and other objects, features and advantages of the invention, will, in part, be pointed out with particularity, and will, in part, become obvious from the following more detailed description of the invention taken in conjunction with the accompanying drawing, which form an integral part thereof.

BRIEF DESCRIPTION OF THE DRAWINGS

In the various figures of the drawing, like reference characters designate like parts. In the drawing:

FIG. 1 is a fragmentary, perspective view on a greatly enlarged scale, illustrating one embodiment of the present invention that is adapted for use in the cultivation of bacteria;

FIG. 2 is a transverse, sectional elevational view taken along line 2—2 of FIG. 1;

FIG. 3 is a greatly enlarged longitudinal sectional view fragmentarily illustrating an alternative embodiment of the present invention;

FIG. 4 is a fragmentary, longitudinal elevational view in section illustrating the embodiment of FIG. 3 at a later stage in the bacteria cultivation process and with additional structure;

FIG. 5 is an enlarged elevational view, partially in section, illustrating additional structure in the form of a dispenser that may be used for example, in conjunction with the embodiments of FIG. 2 and FIG. 3 of the present invention;

FIGS. 5A and 5B schematically represent, on an enlarged scale, alternative embodiments of the dispenser shown in FIG. 5;

FIG. 6 is an elevational view, partially in section, illustrating, on an enlarged scale, another feature of one of the culture dishes shown in the FIG. 5 embodiments;

FIGS. 7A, 7B, 7C, are fragmentary, elevational views in section, illustrating, on enlarged scales, three different conditions of an alternative embodiment of the present invention;

FIGS. 8A and 8B are enlarged, fragmentary, elevational views of a further embodiment of the present invention in two different positions;

FIG. 9 is a fragmentary plan view illustrating, on an enlarged scale, the present invention in the form of an array that is particularly useful in large scale testing;

FIG. 10 is a sectional, elevational view taken along line 10—10 of FIG. 9;

FIGS. 11A, 11B and 11C are enlarged fragmentary, elevational views illustrating three different conditions of still another, alternative embodiment of this invention;

FIG. 12 is an elevational view, on an enlarged scale and in section, which fragmentarily illustrates a typical "double well" culture dish made in accordance with the basic concepts of this invention;

FIG. 13 is an enlarged, fragmentary, perspective view illustrating a dual purpose, double ended tool that is useful with the foregoing embodiments as well as the method of this invention; and FIG. 14 is a plan view of a package for the tool shown in FIG. 13.

DESCRIPTION OF THE PREFERRED EMBODIMENTS

FIG. 1 and FIG. 2 illustrate the basic concept of the present invention. There is shown a strip 10 comprised of upper and lower sheets of synthetic plastic material 12 and 14 which, preferably, are made of an autoclavable material such as polystyrene, by way of example. As will be described hereinafter the upper sheet 12 defines a plurality of covers 16 while the lower sheet 14 defines a plurality of mating culture dishes 18. Intermediate each adjacent cover 16 and mating dish 18 assembly there is provided a transverse line of perforations that define scorelines 20 so that individual pairs of covers 16 and dishes 18 may be separated from the remainder of the strip 10 as required.

Turning particularly to FIG. 2 it will be seen that each cover 16 includes a laterally extending flange portion 22, an upstanding sidewall 24 and a basewall 26. Indicia for identifying the patient may be applied to either the flange portion 22 or the basewall 26 and a knob 27 may be formed integrally with the basewall 26 to aid in the lifting thereof. Similarly, each dish 18 includes a laterally extending flange portion 28, a sidewall 30 having an upper section 32 and a lower section 34, as well as a basewall 36 that defines a receptacle 37 for the culture medium M. As shown by the double line in FIG. 2, the upper section 32 of the sidewall 30 fits loosely within the inside diameter of the sidewall 24 of the cover 16.

Preferably, in the embodiment shown in FIG. 2, the flanges 22 and 28 of the cover 16 and the dish 18, respectively, are heat sealed to each other. A reduced thickness area shown schematically by the reference character 38 may be provided proximate the juncture of the flange 22 and the sidewall 24 of the cover 16 so that using a knob or projection 27, the cover 16 may be readily removed for the purpose of inoculating the culture medium M that is positioned within the receptacle portion 37 of the dish 18. Alternately, a non-secured tab portion 39 may be provided, as shown in FIG. 1, to facilitate the lifting of the flange 22 and the cover 16 from the lower sheet 14. When the cover 16 is replaced after inoculation of the culture medium M, the relatively loose fit between the wall portion 32 of the dish 18 with respect to the wall portion 24 of the cover 16 will permit an indirect flow of air into the dish 18 but will still privent any cross-contamination of the inoculated culture medium M. As an alternative to the heat sealing of the flanges 22 and 28 an adhesive may be used.

FIG. 3 and FIG. 4 illustrate an alternative embodiment of the present invention. It will be noted, particularly in FIG. 3, that the dish 40 includes a flange portion 42, a downwardly depending sidewall 44 and a basewall 46 that defines a receptacle 47 for the culture medium M. An upward extension of the sidewall 44 is absent and in its place there is provided a strippable cover 48 that is secured to the flanges 42 either by heat sealing, by a suitable adhesive or by any other convenient means. As in the first described embodiment, transverse scorelines 50 may also be provided intermediate adjacent dishes 40 so that they may be readily separated. It should be also noted that tabs such as designated by the reference character 39 (FIG. 1) may also be used with the embodiment of FIG. 3.

The embodiment of this invention that is shown in FIG. 3 is used with structure such as shown in FIG. 4. A support place 52, which may be either disposable or sterilizable, is provided with a first plurality of openings 54 for receiving the sidewalls 44 of each dish 40 after the culture medium M in the dish 40 has been inoculated. A second plurality of openings 55 is provided in the support plate 52 for purposes to be described hereinafter. The embodiment of this invention shown in FIG. 4 may be used in the physician's office, in a commercial laboratory or in a research facility. Once the medium M has been inoculated, as described above, a common or simple master cover 56, which may be either disposable or sterilizable, is placed over the open end of the dishes 40. It will be noted that the cover 56 which may also be made of a suitable plastic such as described above is provided with a plurality of locating pins 57 that mate with the second plurality of openings 55. Downwardly depending ribs 58 formed on the underside of the cover 56 fit between the flanges 42 of each two adjacent dishes 40. The ribs 58 rest on the upper surface of the support plate 52. Thus cross-contamination between two adjacent dishes 40 is prevented while sufficient flow of indirect air is permitted. It should be noted at this time that, alternatively, separate covers, which can be either disposable or sterilizable, may be provided for each dish 40 or the master cover 56 shown in FIG. 4 may be utilized. In either event, lifting means shown schematically by projections 59 may be provided. The embodiment of this invention shown in FIG. 1 and in FIG. 2 may also be used with the support plate 52 or it may be used with the embodiment of FIGS. 5 and 6 which will be described hereinafter. Patient identifying indicia may also be applied to an appropriate area of each dish 40 as described hereinabove in connection with the first embodiment.

Turning specifically to FIG. 5 and FIGS. 5A and 5B and to FIG. 6, there are shown still other structures that may be used with various embodiments of the present invention. An elongated, cup-shaped dispenser 60 (FIG. 5) is provided for accommodating a plurality of individual, disposable culture dishes, such as designated by the reference character 40 in FIG. 3, for example. The dishes 40 are stacked one above the other and are supported on a disc 61 and a resilient member such as a compression spring 62 positioned at the bottom of the dispenser 60. A suitable cover 64 is also provided. In the embodiment illustrated in FIG. 5 the cover 64 is slidable by means of an interfitting tongue and groove arrangement or by any other equivalent structure. Alternatively, a hinged cover may be used.

When the cover 64 is moved back the uppermost dish 40 will be exposed and may be removed by the physician. The spring 62 continues to urge the remaining dishes 40 upwardly. After inoculation, in the manner described hereinabove, the dishes 40 may be returned to the dispenser 60 so that they may be transported back to the physician's office or to the laboratory for incubation. In the embodiment shown in FIG. 5 the dishes 40 are provided with a reusable cover 66 (FIG. 6) which is peeled back at least partially when the culture medium M in the dish 40 is to be inoculated and which is replaced prior to being returned to the dispenser 60. Once the inoculated dishes 40 are returned to either the physician's office or the laboratory, the system shown in FIG. 4 may be utilized for incubation purposes. That is, the cover 66 of each dish 40 is permanently removed and is replaced by either the master cover 56 or by individual covers that permit the inflow of indirect air without permitting cross-contamination during incubation.

FIGS. 5A and 5B schematically represent alternative dispenser constructions. For example, in FIG. 5A the dispensers 60' and 60" are back-to-back or end-to-end. Like reference characters with prime and double prime superscripts represent like parts. The sterile dishes 40' are taken from the dispenser 60' and, after inoculation, are returned to the dispenser 60" for subsequent transport. In the embodiment of FIG. 5B the dispensers 60a and 60b are side-by-side. Like reference characters with subscripts a and b represent like parts. The sterile dishes 40a are taken from the dispenser 60a and are returned to the dispenser 60b for subsequent transport. The covers 64a and 64b may have a common hinge connection 68.

Referring now to FIGS. 7A, 7B, and 7C there is shown a further embodiment of the present invention. In this last mentioned embodiment a culture dish 70 is comprised of a basewall 72 having a lateral extension 74 and a sidewall 76 extending upwardly from the basewall 72 thereby defining a receptacle 77 for the culture medium M. The outside surface of the wall 76 is provided with a pair of axially spaced apart, outwardly or radially extending upper and lower ribs 78 and 80, respectively. The upper rib 78 has upper and lower surfaces 82 and 84 respectively, while the lower rib 80 is provided with upper and lower surfaces 86 and 88, respectively.

A cover 90 for the culture dish 70 shown in the FIG. 7 embodiment is comprised of a transverse wall 92 having lifting means 93 extending upwardly therefrom, a sidewall 94 depending downwardly therefrom and a rib 96 extending inwardly from the wall 94. Suitable patient identifying indicia may be applied to the wall 92. The rib 96 has upper and lower surfaces 98 and 100, respectively. At the lower end of the wall 94 there is provided a laterally extending flange 102 that is in contact with the flange 74 of the dish 70. The outer surface of the sidewall 94 is further provided with a reduced thickness portion 104. Prior to usage the culture medium M is positioned within the receptacle portion 77 of the dish 70 and the flanges 102 and 74 are secured to each other such as by heat sealing, by a suitable adhesive or by other equivalent means. In this condition, and as shown in FIG. 7A, the lower surface 100 of the rib 96 on the cover 92 rests on the upper surface 82 of the upper rib 78 formed integrally with the dish 70. In this condition, the sterile culture medium M can be safely stored and transported.

Just prior to usage, by either the physician or the laboratory technician, the seal is broken between the flanges 102 and 74 and the lower section of the sidewall 94 is broken off at the reduced thickness portion 104 thereof. The culture medium M is then inoculated in the manner set forth above and then the cover 90 is immediately replaced over the dish 70. As shown in FIG. 7B the rib 96 of the cover 90 will be snapped over the rib 78 of the dish 70 and will be positioned between the lower face 84 of the upper rib 78 and the upper face 86 of the lower rib 78. In this position the cover will be securely held in place during transport.

During incubation, such as is shown in FIG. 7C, the cover 90 is once again removed and the rib 96 that is integral therewith is positioned with the lower face 100 thereof resting on the upper face 82 of the upper rib 80 that is formed integrally with the dish 70. In this condition there will be a free flow of indirect air into the inoculated culture medium M but there will be little likelihood of cross-contamination from any adjacent dish. After the analysis is completed the cover 90 may be pushed down again to the position shown in FIG. 7B so that the dish 70 and the cover 90 may be disposed of as a unit.

Still another embodiment of the present invention is disclosed in FIG. 8A and in FIG. 8B. In this last mentioned embodiment there is provided a culture dish 110 which is comprised of a basewall 112 having a sidewall 114 extending upwardly therefrom to thereby define a receptacle 115 for the culture medium M. A transverse flange 116 extends radially or outwardly from the upper end of the sidewall 114. The flange 116 is provided with a transverse top surface 118 that also extends in a radial or outward direction, a peripheral sidewall section 120 that extends in an axial direction and downwardly from the top surface 118 and a radially or outwardly extending wall portion 122 which extends from the sidewall section 120. A fluid impervious seal 124 may also be used and, if it is, the seal 124 is suitably secured to one or more of the surfaces 118, 120 and 122. There is also provided a cover generally designated by the reference character 126 that is comprised of a transverse top wall 128 having a first sterile surface 128a, and a second surface 128b and an annular, axially extending sidewall 130 that is integral with the radially outer end of the top wall 128. A flange 132 extends radially or outwardly from the annular wall 130. A strippable sheet 134 is positioned over the top wall 128 of the cover 126 in order to maintain the integrity of the sterilized surface 128a thereof.

When the culture medium M within the receptacle portion 115 of the dish 110 is to be inoculated, the cover 126 is removed together with the fluid impervious seal 124 and inoculation is carried out as described above. Once this is done the sheet 134 is removed and the cover 126 is inverted (FIG. 8B) so that the end of the annular wall 130 of the cover 126 rests against the flange 122 and the side 120 of the flange 116 of the dish 110. The sterile surface 128a of the cover 126 is then in opposition to the culture medium M. In this manner a free flow of air is permitted to the interior of the dish 110 and yet the sterile condition is maintained so as to prevent any contamination of the culture medium M in the receptacle 115. Patient identifying indicia may be applied to the second and now outwardly directed surface 128b of the cover 126.

The embodiment of this invention shown in in FIG. 9 and in FIG. 10 utilizes the basic concepts described in connection with the previously discussed embodiments and is particularly useful for large scale testing, such as may be done in a commercial laboratory or in a research facility. There are provided upper and lower sheets 140 and 142 that are sealed to each other, for example along their mating, marginal edges. The reference character 144 indicates either a heat seal, an adhesive or any other comparable seal means.

The upper sheet 140 shown in FIG. 9 and in FIG. 10 includes a plurality of covers 146 each of which is defined by a transverse wall 148 and a sidewall 150 extending downwardly therefrom. Similarly, the lower sheet 140 includes a plurality of separate dishes or wells 152 each of which is defined by a basewall 154 and a sidewall 156 extending upwardly therefrom. The culture medium M is contained in the receptacle portion 157 which is defined by the wells 152.

When the seal 144 is broken the upper sheet 140 is removed and the culture medium M is inoculated in the usual manner. The upper sheet 140 is then replaced. It will be noted that the sidewalls 156 of each well 152 nests within the sidewalls 150 thus permitting the inflow of air while preventing cross-contamination. The upper and lower sheets 140 and 142 represent a completely self-contained plurality of culture dishes and are self supporting thereby eliminating the need for additional support means either during storage, inoculation for incubation.

Turning now to FIGS. 11A, 11B and 11C there is shown an embodiment of this invention that represents a combination of the concepts shown in FIGS. 7 and 8. That is, the cover is initially snapped into engagement with the dish in order to maintain sterility and is inverted after inoculation in order to permit incubation.

As shown in FIG. 11A for example, there is provided a culture dish 160 that includes a basewall 162 having a sidewall 164 extending upwardly therefrom for defining a receptacle 166 for the culture medium M. A circumferential, radially or outwardly extending rib 168 having an outer surface 170 is formwed integrally with the sidewall 164 intermediate the ends thereof. The end 172 of the sidewall 164 that is remote from the basewall 162 may be provided with a minimum surface area and a lip 174 is also formed adjacent the end 172 of the sidewall 164.

A cover generally designated by the reference character 180 is provided for the culture dish 160. The cover 180 is comprised of a transverse wall 182 having axially extending side wall portions 184 and 186 extending upwardly and downwardly, respectively, from the radially outer end thereof. The downwardly extending side wall portion 186 is substantially coplanar with the outer surface 170 of the side wall 164 of the culture dish 160 so that the two surfaces 170 and 188 may receive a removable sealing strip 190 that joins the culture dish 160 and the cover 180 therefore as shown in FIG. 11A. A radially inwardly directed lip 192 is also formed on the downwardly extending side wall portion 186 so as to coact with the lip 174 formed on the sidewall 164 of the culture dish 160. Finally, a strippable sheet 194 is positioned over the surface 182a of the transverse wall 182. Surface 182b of the transverse wall 182 may be used for patient identifying indicia.

Initially the strip 190 and the interfitting of the lips 174 and 192 joins the culture dish 160 and the cover 180 and thereby maintains the sterility of the culture medium M. After the strip 190 is removed (FIG. 11B) the cover 180 can be taken off and the culture medium M can be inoculated. The sheet 194 is then removed, the cover 180 is inverted and the sterile surface 182a of the transverse wall 182 is placed on the end 172 of the sidewall 164. The culture medium M which has been incubated as described hereinbefore will be provided with a flow of indirect air as a result of the minimum contact between the end 172 of the sidewall 164 and the sterile surface 182a of the transverse wall 182. Since the sidewall 164 of the culture dish 160 nests loosely within the downwardly extending sidewall portion 186 of the cover 180, cross-contamination between adjacent culture dishes is minimized.

In FIG. 12 there is shown separately a feature of this invention that may be applied to any of the previously described embodiments which have each been illustrated with a single well or receptacle in the culture dish portion. By way of contrast FIG. 12 schematically illustrates a typical culture dish 200 having a "double well" construction. The culture dish 200 is comprised of a base wall 202, an integral side wall 204 and an internal partition wall 205 that defines a pair of receptacles 206 and 208. Thus, it is possible to place a diluent D in the receptacle 206 and the culture medium M in the receptacle 208. A cover 210 is provided for the receptacles 206 and 208 of the culture dish 200. At this time it should be particularly noted that the drawing of FIG. 12 is intended for illustrative purposes only and that the culture dish 200 and the cover 210 may be of any of the previously described configurations.

Turning now to FIGS. 13 and 14 there is shown a combination disposable swab and loop 220 that may be used with the foregoing embodiments. The combination swab and loop 220 is comprised of a rigid plastic, elongated stem 222 having a cotton swab 224 secured to one end thereof and a loop 226 formed integrally with the other end thereof. The swab 224 which may also be made of other suitable material, is used for collecting inoculum in the patient's throat and is then placed in the diluent D which is usually the same as the culture medium M but without the agar. The loop 220 is first placed in the diluent D and is then placed in the culture medium M for inoculation purposes.

A package 230 such as shown in FIG. 14 may be used for the combination swab and loop 220. The package 230 is comprised of upper and lower plastic sheets 232 and 234, respectively, which are heat sealed or otherwise secured to each about a martinal, peripheral edge 236. Additionally, a second transverse seal 238 is provided for defining two separate compartments 240 and 242. It will be appreciated that the two compartments 240 and 242 are opened one at a time. That is, the compartment 240 is opened just prior to the use of the swab 224 and the compartment 243 is opened just prior to the use of the loop 226. To facilitate partial opening of the package in order to expose the compartments 240 and 242, one at a time, a score line 244 may be provided.

In each of the foregoing embodiments it is contemplated that the culture dish will have a diameter in the order of 5mm. – 10 mm., a depth in the order of 5 mm. – 10 mm. and will contain a culture medium having a depth in the order of 2.5 mm. – 5 mm. While circular culture dishes have been illustrated, it should be clearly understood that the invention is not limited to that shape and in fact, the culture dishes may be either square, rectangular or any other convenient shape. When a liquid culture medium is used the depth of the dish will be greater than the width of the dish.

From the foregoing it will be appreciated that an improved miniaturized, microbiological culture system has been provided. The present invention permits convenient storage, transport and incubation of the disposable, plastic culture dish and cover and does not sacrifice the sterility of the culture medium therein. The present invention lends itself readily to mass production testing techniques through the use of a common support plate which is used in conjunction with a master cover and also finds utility for individual testing such as may be carried out by a physician, either in his office or in the patient's home. An improved dispenser has also been disclosed for carrying a relatively large number of culture support devices and for providing transport means thereof.

Although the invention has heretofore been described in connection with a miniaturized apparatus, the invention can also be utilized with conventional sized apparatus. Thus, there would be provided a conventional microbiological assembly with a cover and dish as described in any one of the embodiments which would provide an individualized sterile culture medium for inoculation and incubation.

There has been disclosed heretofore the best embodiments of the invention presently contemplated. However it is to be understood that various changes and modifications may be made thereto without departing from the spirit of the invention.

What I claim as new and desire to secure by Letters Patent is:

1. An autoclavable, miniaturized microbiological assembly that is readily transportable both before and after innoculation, said assembly comprising:

a. a dish having at least one well therein;
   b. a pre-packaged, sterile culture medium contained within said well;
   c. removable cover means mounted on said well;
   d. cooperating portions on said dish and on said cover means for defining three separate and distinct physical arrangements of said dish and said cover means with respect to each other, said cooperating portions including integral frangible sealing means for sealing securely said cover means to said dish to define said first arrangement whereby said well is closed and said medium is maintained in a sterile condition prior to the introduction of the bacteria, said second arrangement being such that subsequent contamination of the medium after introduction of bacteria thereto is prevented while only an indirect flow of air to the medium and the bacteria is permitted; and said third arrangement being such that said cover means is temporarily coupled to said dish after introduction of the bacteria and prior to permitting the flow of indirect air thereover to thereby permit transport of said assembly in an unsealed condition without contamination of the medium said integral frangible sealing means being broken in said second and third arrangements.

2. The assembly according to claim 1 wherein said sealing means comprises flange means on said cover means and said dish, said flange means including a frangible area of reduced thickness, said flange means being secured to each other whereby said cover means is removable for the purpose of introduction of the bacteria and replaceable for the cultivation of the bacteria.

3. The assembly according to claim 1 wherein there are a plurality of said assemblies in the form of a strip and wherein there is further included means for separating adjacent assemblies from each other.

4. The assembly according to claim 1 wherein said dish is defined by a first, peripheral flange and a wall portion extending upwardly therefrom, said cover means being defined by a second, peripheral flange and a recess for receiving said wall portion of said dish.

5. The assembly according to claim 1 wherein said cover means includes a projection permitting the gripping thereof.

6. The assembly according to claim 1 wherein said cover means includes an area for the addition of patient identifying indicia.

7. The assembly according to claim 1 wherein there is further included a master support rack having a plurality of openings for receiving a plurality of said dishes and wherein said cover means of each said dish is in the form of a sheet that is adapted to be replaced; said cover means further comprising a master cover for replacing said sheet and for closing all said dishes, said master cover including said cooperating portions.

8. The assembly according to claim 7 wherein said master support rack and said master cover include cooperating registration means that substantially prevent relative lateral movement therebetween.

9. The assembly according to claim 1 wherein said dish is defined by a basewall having a flange extending outwardly therefrom and a sidewall extending upwardly therefrom, said sidewall including at least one outwardly extending rib, said cover means being defined by an end wall, a sidewall extending downwardly therefrom and positioned outwardly of said dish sidewall and a flange extending outwardly from the end of said cover sidewall that is remote from said end wall, said cover sidewall including at least one inwardly extending rib, said flanges being releasably secured to each other with said cover rib being positioned above said dish rib prior to the introduction of the bacteria, said cover rib being adapted to be positioned below said dish rib after said flanges are separated from each other and the bacteria is introduced and prior to the cultivation of the bacteria, said cover rib being adapted to be positioned over said dish rib during cultivation of the bacteria.

10. The assembly according to claim 9 wherein said cover side wall includes an area of reduced thickness permitting rupture thereof and removal of said side wall below said reduced thickness area together with the removal of said cover flange prior to introduction of the bacteria.

11. The assembly according to claim 9 wherein said dish side wall includes two axiallyspaced apart outwardly extending ribs and said cover rib is adapted to be positioned therebetween after introduction of the bacteria and before the cultivation thereof.

12. The assembly according to claim 1 wherein there is further included a removable, fluid impervious seal intermediate said dish and said cover means.

13. The assembly according to claim 1 wherein said cover means further includes an outwardly directed sterile surface on said end wall and a strippable sheet covering said sterile end wall surface, said cover means being invertible whereby in a first position thereof and at a time prior to the introduction of the bacteria into the medium said sterile end wall surface faces outwardly and is covered by said sheet and whereby in a second position of said cover means said sheet is removed and said sterile end wall surface faces inwardly to thereby permit the indirect flow of air to the bacteria in the medium.

14. The assembly according to claim 1 wherein there is further included external tear strip means for releasably securing said dish to said cover means.

15. The assembly according to claim 1 wherein there are a plurality of said dishes formed on a first sheet and a plurality of said cover means formed on a second sheet and seal means are provided for securing said first and said second sheets to each other in an area outward of said dishes and said cover means.

16. The assembly according to claim 1 wherein each said dish includes a partition wall for separating said well into first and second compartments whereby said first compartment is adapted to contain a diluent and said second compartment is adapted to contain the sterile medium.

17. The assembly according to claim 16 wherein there is further included a double ended member having a swab at one end and a loop at the other end whereby said swab is adapted to collect the inoculum and place it in the diluent and said loop is adapted to transfer a portion of the inoculated diluent to the medium.

18. The assembly according to claim 17 wherein there is further included a sterile package having a first compartment for receiving said swab and a second compartment for receiving said loop.

19. The assembly according to claim 18 wherein there is further included means for permitting the selective opening of said compartments.

20. The assembly according to claim 1 wherein there is further included dispensing means for a plurality of said dishes and corresponding cover means arranged in a stack, said dispensing means comprising:
 a. at least one housing means;
 b. displaceable cover means for said housing means; and
 c. means for normally biasing said plurality of dishes and corresponding cover means in at least a first direction, whereby when said displaceable cover is moved from the housing means the uppermost dish and corresponding cover means is exposed for removal from said housing means.

21. The assembly according to claim 20 wherein there are at least two of said housing means in side by side arrangement.

22. The assembly according to claim 20 wherein said housing means includes a central divider for defining two separate stacks of said dishes and corresponding cover means and wherein there are at least two of said biasing means acting in two opposing directions, each of said biasing means acting upon a separate one of said stacks.

23. A method for cultivating bacteria in a sterile dish having a frangible seal means and a cover means comprising the steps of:
 a. breaking off and unsealing the frangible seal means from the cover means and the sterile dish having a medium therein;
 b. introducing bacteria into the medium;
 c. temporarily placing the cover means on the dish in an unsealed condition for preventing contamination of the medium; and
 d. thereafter positioning the cover means in a position different from that of step (c) to provide an indirect flow of air to the bacteria and the medium to thereby permit cultivation of the bacteria.

24. The method according to claim 23 wherein step (c) comprises placing the cover means on the dish in a first position and step (d) comprises inverting the cover means and placing it on the dish in a second position.

25. The method according to claim 23 wherein said unsealing step comprises removing an external seal strip.

26. The method according to claim 23 wherein said unsealing step comprises removing a sterile sheet positioned intermediate the dish and the seal means.

27. The method according to claim 23 wherein said introducing step comprises placing the inoculum into a diluent and then transferring a portion of the diluent to the medium, the diluent and the medium being contained in separate compartments in the dish.

* * * * *